United States Patent [19]

Ibe

[11] 4,132,227
[45] Jan. 2, 1979

[54] UROLOGICAL ENDOSCOPE PARTICULARLY RESECTOSCOPE

[75] Inventor: Wolfgang Ibe, Hamburg, Fed. Rep. of Germany

[73] Assignee: Winter & Ibe, Hamburg, Fed. Rep. of Germany

[21] Appl. No.: 812,177

[22] Filed: Jul. 1, 1977

Related U.S. Application Data

[63] Continuation of Ser. No. 602,400, Aug. 6, 1975, abandoned.

[30] Foreign Application Priority Data

Aug. 8, 1974 [DE] Fed. Rep. of Germany ... 7426959[U]

[51] Int. Cl.$^2$ .............................................. A61B 1/00
[52] U.S. Cl. ........................................ 128/4; 128/240; 128/248; 128/303.15; 128/7
[58] Field of Search ........................................ 128/4–8, 128/235–241, 276, 303.15, 248–251

[56] References Cited

U.S. PATENT DOCUMENTS

| | | | |
|---|---|---|---|
| 1,638,532 | 8/1927 | Kallmayer | 128/239 |
| 3,835,842 | 9/1974 | Iglesias | 128/303.15 |
| 3,850,175 | 11/1974 | Iglesias | 128/303.15 |

*Primary Examiner*—Robert W. Michell
*Assistant Examiner*—Henry S. Layton
*Attorney, Agent, or Firm*—Michael J. Striker

[57] ABSTRACT

A hollow cylindrical sheath has a proximal end and a distal end. An optical viewing device is located in the sheath extending from the distal back to the proximal end. An outflow tube is slidable onto the sheath to surround the sheath and form together with the sheath an intermediate return-flow space between the outer wall of the sheath and the inner wall of the outflow tube, with the outflow tube when in position slid over the sheath tightly surrounding the distal end portion of the sheath. Clear rinsing water is introduced into the proximal end of the sheath. Turbid water is removed from the proximal end of the intermediate space. The outflow tube is provided with apertures at the distal end thereof for the flow of clear rinsing water out of the distal end of the sheath and around the end of the endoscope and then through the apertures into the intermediate space.

6 Claims, 6 Drawing Figures

UROLOGICAL ENDOSCOPE PARTICULARLY RESECTOSCOPE

CROSS-REFERENCE TO RELATED APPLICATIONS

The present application is a continuation of my co-pending application Ser. No. 602,400, filed Aug. 6, 1975, now abandoned.

BACKGROUND OF THE INVENTION

The invention relates to urological endoscopes, particularly resectoscopes, of the type comprised of a hollow cylindrical sheath through which passes, besides an endoscopic optical viewing arrangement, and possibly also an operating instrument (such as a loop-shaped resecting electrode), clear rinsing water, and provided with means for effecting the return flow of the rinsing water discharged from the distal end of the endoscope.

Resectoscopes are most often used to remove pathological tissue from the prostate gland. For this purpose, the sheath of the resectoscope must be inserted into the urethra to such an extent that the distal end of the sheath, and the reciprocating resecting electrode loop therein, are located in the operating zone. To make the field of view clear during the resecting operation in the case of electroresection, clear rinsing water is fed into the operating zone through the resectoscope sheath. The clear rinsing water, made turbid as a result of becoming mixed with blood at the operating zone, is removed from the operating zone by suitable means. With known constructions, there is provided, for the purpose of effecting the removal of the turbid rinsing water, a return-flow conduit disposed inside the resectoscope sheath extending all the way to the distal end of the resectoscope sheath and of course having a diameter considerably smaller than that of the resectocope sheath. Such an arrangement of the return-flow conduit for the rinsing water complicates to a considerable degree the cleaning of the resectoscope. Additionally, the rinsing effect, provided for the purpose of making clear the field of view, is less than satisfactory, because the clear rinsing fluid discharged from the distal end of the resectoscope sheath for the most part is directly diverted into the inflow port of the return-flow conduit, so that sizable amounts of the rinsing fluid in the bladder, made turbid by mixture with blood, do not actually enter the return-flow conduit.

SUMMARY OF THE INVENTION

It is a general object of the invention to provide an endoscope or resectoscope which avoids these disadvantages, i.e., which improves the field of vision in the operating zone, and which is markedly easier to clean than the arrangements known in the prior art.

These objects, and others which will become more understandable from the description below, of preferred embodiments, can be met, according to one advantageous concept of the invention, by making the distal end of the endoscope or resectoscope sheath of enlarged diameter, and by providing an outflow tube slidable over the sheath, the outflow tube having an inner diameter corresponding to the outer diameter of the enlarged distal end portion of the sheath. When the outflow tube is slid onto and over the sheath, its distal end lies directly against and tightly surrounds the enlarged distal end portion of the endoscope or resectoscope sheath, whereas the proximal end of the outflow tube can be coupled with the base of the endoscope or resectoscope sheath and is provided with an outflow connection. In the wall of the outflow tube, near the distal end thereof, there are provided apertures which open into the intermediate space defined between the inner wall of the outflow tube and the outer wall of the endoscope or resectoscope sheath.

One advantage of the invention is that the return-flow conduit constituted by the intermediate space between the inner wall of the outflow tube and the outer wall of the endoscope or resectoscope sheath is of relatively large cross-sectional area. When the outflow tube is slid off the endoscope or resectoscope sheath, both the outflow tube interior and the sheath exterior can be cleaned very easily.

Another advantage of the invention is that the clear rinsing water discharged from the distal end of the endoscope or resectoscope sheath is constrained to flow around the edges of the distal end of the sheath and back through the apertures in the wall of the outflow tube, into the interior space which serves as the return-flow conduit. In this way, the clear rinsing water discharged into the operating zone in effect forces the turbid water already present there to be caught up in the main stream of the circulation and enter through the apertures into the intermediate return-flow space. As a result, there is much less of a tendency for the clear rinsing water to be immediately diverted back into the return-flow space without actually passing through the operating zone. This greatly improves the visibility within the operating zone.

However, even resorting to the expedients just mentioned, there is the danger that the portion of the outflow tube provided with the apertures in question will become tightly surrounded by the prostate or by the wall of the urethra itself, so as to block off the return-flow apertures. This could make impossible the return flow of rinsing water, resulting in dangerous pressure build-ups within the bladder. To prevent this, if the distal end of the endoscope or resectoscope sheath is provided with a beak portion inserted into the distal end of the sheath, with the outflow tube likewise having a beak-shaped distal end portion, then the beak-shaped end of the outflow tube surrounds the beak of the sheath and is provided with an outwardly projecting, longitudinally extending, hollow ridge extending back into the intermediate space between the outflow tube and the sheath and provided on its two flanks with apertures. This outwardly projecting, longitudinally extending, hollow ridge, if surrounded by the wall of the urethra or by tissue of the prostate, pushes the surrounding tissue outwardly away from the outflow tube, so that alongside the flanks of the hollow ridge the tissue does not press against the flanks but instead leaves free spaces through which the turbid rinsing water can gain access into the return-flow intermediate space through the apertures.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
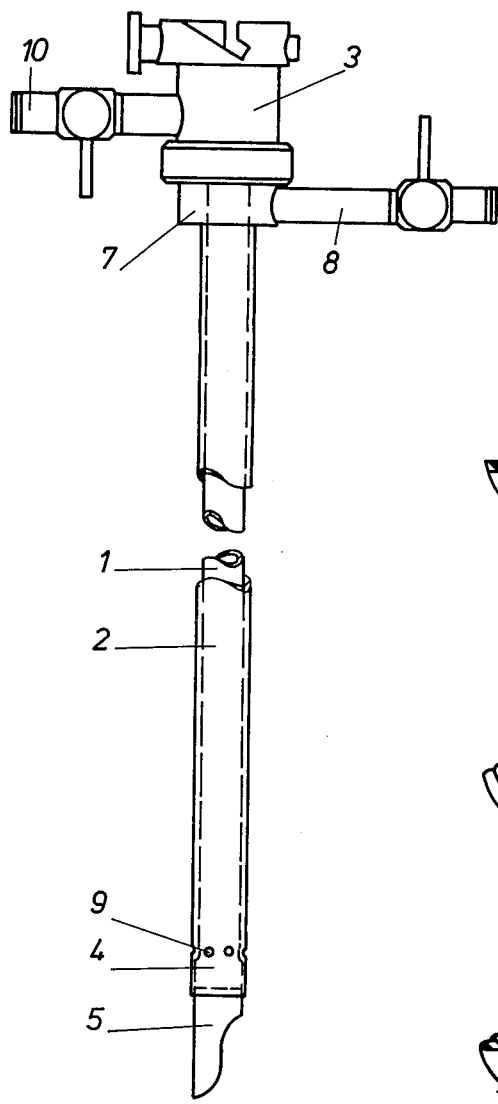
FIG. 1 depicts a resectoscope, particularly a resectoscope sheath surrounded by a slide-on outflow tube.
Figure 5:
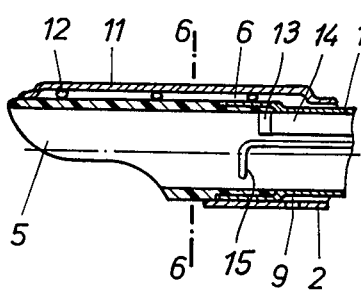
FIG. 5 is a longitudinal section through the structure shown in FIG. 4.
Figure 6:
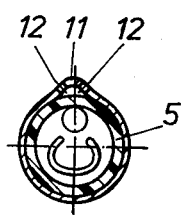
FIG. 6 is a section taken on line 6—6 of FIG. 5.

In FIG. 1 there is depicted the sheath 1 of a resectoscope. Slid over and onto the resectoscope sheath 1 is an outer outflow tube 2. The sheath 1 at is proximal end is provided with a base 3 which can be coupled in non-illustrated and per se conventional manner with the main part of the resectoscope. After connecting the sheath 1 to the main part of the resectoscope, there are inserted into the sheath 1 the endoscope optic (for example a lens arrangement 13 and a cooperating fiber-optic arrangement 14 such as shown in FIGS. 5 and 6) and also energizing conductors for the resecting electrode loop (such as 15 shown in FIGS. 5 and 6). In per se conventional manner, the resecting electrode is caused to axially reciprocate by manipulation of an activating mechanism provided at the (non-illustrated) main part of the resectoscope.

The hollow sheath 1 at its distal end is of enlarged diameter, and this large-diameter portion receives a beak-shaped insert 5 made of dielectric material. The outflow tube 2 has an inner diameter which corresponds to the outer diameter of the large-diameter portion 4 and of the beak 5.

Figure 2:
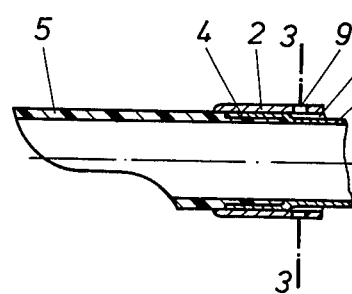
FIG. 2 is a longitudinal section through the structure of FIG. 1, on a larger scale.
Figure 3:
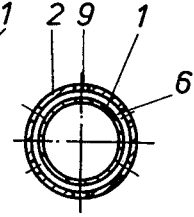
FIG. 3 is a section taken along line 3—3 of FIG. 2.

When the outflow tube 2 is slid over and onto the sheath 1, the distal end of the outflow tube 2 seal-tightly surrounds the larger-diameter portion 4 of the sheath 1. Rearwards of this portion of the sheath 1, as seen particularly clearly in FIG. 2, the outflow tube 2 and sheath 1 together define an intermediate space between the inner wall of the outflow tube and the outer wall of the sheath.

The proximal end of the outflow tube 2 is provided with a connector unit 7 so that the outflow tube 2 can be secured to the base 3 of the sheath 1 in such a manner that the proximal end of the intermediate space 6 is sealed off. Turbid rinsing fluid is withdrawn from the proximal end of the intermediate space 6 via an outflow connector 8 provided on the connector unit 7. At the distal end of the outflow tube 2 apertures 9 are provided in the wall of the outflow tube, opening into the intermediate space 6.

Prior to a surgical procedure, the sheath 1, with the outflow tube 2 slid onto the over the sheath 1, and with the outflow tube locked onto the base 3 by means of the connector unit 7, is slid into the urethra. Thereafter, the endoscope optical arrangement and the resecting electrode arrangement are slid into the sheath 1. The supply conductors of the electrode arrangement extend into the (non-illustrated) main part of the resectoscope and are connected to a (non-illustrated) source of electrical energy. The base 3 of sheath 1 is locked onto the main part of the resectoscope after the parts just mentioned have been inserted.

The operating zone, located in the region of the beak 5, is then illuminated by light transmitted by the fiber optic means 14 from a non-illustrated light source and can be observed by the surgeon. The surgeon then manipulates the activating device on the (non-illustrated) main part of the resectoscope, in per se conventional manner, to effect the longitudinal reciprocation of the resecting electrode required to excise pathological tissue.

In order to clear the operating zone of turbid rinsing water which if not removed would detract from the visibility of the operating zone, clear rinsing water is introduced into an inflow connector 10 at the base 3 of the sheath 1, and flows to the distal end of the resectoscope sheath 1, where it is discharged into the operating zone. The thusly discharged clear rinsing water forces the already present turbid rinsing water to flow through the apertures 9 into the intermediate space 6 to the proximal end of the outflow tube 2, whereupon it is removed via the outflow connector 8.

Figure 4:
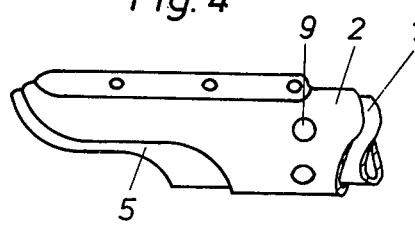
FIG. 4 is a side view of the distal end of the resectoscope when provided with an outflow tube of different configuration.

In the embodiment of FIGS. 4–6, the distal end of the outflow tube 2 is beak-shaped and, after it has been slid onto the sheath 1, surrounds the beak 5, the beak 5 as already explained being inserted into the larger-diameter end portion of the sheath 1. This beak-shaped end portion of the outflow tube is provided with a longitudinally extending, outwardly projecting, hollow ridge 11. The ridge 11 extends at its distal end up to the vicinity of the edge of the beak-shaped end of the outflow tube and at its proximal end back into the main portion of the intermediate space between the outflow tube 2 and sheath 1. The hollow ridge 11 has two flanks provided with apertures 12. If the distal end of the outflow tube 2 is tightly surrounded by the wall of the urethra or by the tissue of the prostate, this could conceivably block the apertures leading into the intermediate space 6 and dangerously prevent the return-flow of the rinsing water. This is prevented by the ridge 11. The rigde 11 presses the tissue away from the outflow tube 2 to create clearances along the two flanks of the ridge 11, permitting entry of rinsing water into the apertures 12. To this end the ridge 11, if necessary or desired, can project outwards to a greater extent than shown.

It will be understood that each of the elements described above, or two or more together, may also find a useful application in other types of constructions differing from the types descrbed above.

While the invention has been illustrated and described as embodied in a urological endoscope, and particularly a resectoscope, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A urological endoscope, comprising, in combination, a hollow cylindrical sheath having a proximal end and a distal end, said sheath comprising a beak at its distal end; optical viewing means in said sheath extending from said distal end back towards said proximal end; a removable outflow tube slidable onto the sheath to surround said sheath and form together with said sheath an intermediate return-flow space between the outer wall of said sheath and the inner wall of said outflow tube, said outflow tube when in position over said sheath tightly surrounding said distal end of said sheath; means for introducing clear rinsing water into the proximal end of said sheath; and means for withdrawing turbid water from the proximal end of said intermediate space, said outflow tube being provided with apertures at the distal end thereof, said apertures being located distally of the distal end of said optical viewing means but proximally of the distal end of said outflow tube so that said apertures open directly into said intermediate space for the flow of clear rinsing water out of the distal end of said sheath and around the end of the endoscope and then through said apertures directly into said intermediate space.

2. An end scope as defined in claim 1, wherein said distal end of said sheath is of widened diameter, and wherein the distal end of said outflow tube tightly surrounds only that portion of said sheath which is of widened diameter leaving said intermediate space rearwards of said widened-diameter portion of said sheath, the inner diameter of the distal end of said outflow tube corresponding to the outer diameter of the tightly surrounded portion of said sheath.

3. An endoscope as defined in claim 1, and further including resecting electrode means inside said sheath at the distal end thereof and energizing means extending from said resecting electrode means to said proximal end of said sheath.

4. A urological endoscope, comprising, in combination, a hollow cylindrical sheath having a proximal end and a distal end; said sheath comprising a beak at its distal end; optical viewing means in said sheath extending from said distal end back towards said proximal end; a removable outflow tube slidable onto the sheath to surround said sheath and form together with said sheath an intermediate return-flow space between the outer wall of said sheath and the inner wall of said outflow tube, said outflow tube when in position over said sheath tightly surrounding said distal end of said sheath; means for introducing clear rinsing water into the proximal end of said sheath, and means for withdrawing turbid water from the proximal end of said intermediate space, said outflow tube being provided with apertures at the distal end thereof, said apertures being located distally of the distal end of said optical viewing means by proximally of the distal end of said outflow tube so that said apertures open directly into said intermediate space for the flow of clear rinsing water out of the distal end of said sheath and around the end of the endoscope and then through said apertures directly into said intermediate space, wherein said sheath is provided with an end beak at said distal end, and wherein the distal end portion of said outflow tube terminates rearwardly of said beak, wherein said distal end of said sheath is of enlarged diameter, and wherein said beak is an insert received within the enlarged distal end portion of said sheath.

5. A urological endoscope, comprising, in combination, a hollow cylindrical sheath having a proximal end and a distal end; said sheath comprising a beak at its distal end; optical viewing means in said sheath extending from said distal end back towards said proximal end; a removable outflow tube slidable onto the sheath to surround said sheath and form together with said sheath an intermediate return-flow space between the outer wall of said sheath and the inner wall of said outflow tube, said outflow tube when in position over said sheath tightly surrounding said distal end of said sheath; means for introducing clear rinsing water into the proximal end of said sheath; and means for withdrawing turbid water from the proximal end of said intermediate space, said outflow tube being provided with apertures at the distal end thereof, said apertures being located distally of the distal end of said optical viewing means but proximally of the distal end of said outflow tube so that said apertures open directly into said intermediate space for the flow of clear rinsing water out of the distal end of said sheath and around the end of the endoscope and then through said apertures directly into said intermediate space, wherein said distal end of said outflow tube extends to the distal end of said sheath, and wherein said distal end portion of said outflow tube is provided with an outwardly projecting hollow ridge provided on its flanks with said apertures, whereby if the wall of the urethra tightly surrounds the distal end of the endoscope the outwardly projecting hollow ridge will distend a portion of the urethra creating clear space adjoining said flanks and establishing access into said apertures for turbid rinsing water.

6. A urological endoscope, comprising, in combination, a hollow cylindrical sheath having a proximal end and a distal end, said sheath comprising a beak at its distal end; optical viewing means in said sheath extending from said distal end back towards said proximal end; a removable slide-on outflow tube slidable onto the sheath to surround said sheath and forming together with said sheath, when slid into place around said sheath, an intermediate return-flow space between the outer wall of said sheath and the inner wall of said slide-on outflow tube, said outflow tube when in position over said sheath tightly surrounding said distal end of said sheath; means for introducing clear rinsing water into the proximal end of said sheath; and means for withdrawing turbid water from the proximal end of said intermediate space, said outflow tube being provided with apertures at the distal end thereof, said apertures opening directly into said intermediate space for the flow of clear rinsing water out of the distal end of said sheath and around the end of the endoscope and then through said apertures directly into said intermediate space.

* * * * *